(12) United States Patent
Tsai

(10) Patent No.: US 6,752,784 B2
(45) Date of Patent: Jun. 22, 2004

(54) LABOR EFFICIENT SAFETY SYRINGE

(76) Inventor: Hsi-Chin Tsai, 2nd Fl., No. 524, Ta-An Rd., Shulin City, Taipei Hsien (TW)

( * ) Notice: Subject to any disclaimer, the term of this patent is extended or adjusted under 35 U.S.C. 154(b) by 170 days.

(21) Appl. No.: 10/208,625

(22) Filed: Jul. 30, 2002

(65) Prior Publication Data

US 2004/0024366 A1 Feb. 5, 2004

(51) Int. Cl.⁷ .............................. A61M 5/00; A61M 5/32
(52) U.S. Cl. ........................................ 604/110; 604/197
(58) Field of Search ................................ 604/110, 195, 604/197, 198, 240, 243

(56) References Cited

U.S. PATENT DOCUMENTS

| | | | | |
|---|---|---|---|---|
| 6,093,171 A | * | 7/2000 | Huang | 604/110 |
| 6,193,687 B1 | * | 2/2001 | Lo | 604/110 |
| 6,391,008 B1 | * | 5/2002 | Tsai | 604/195 |
| 6,468,246 B1 | * | 10/2002 | Lo | 604/110 |

\* cited by examiner

*Primary Examiner*—Michael J. Hayes
(74) *Attorney, Agent, or Firm*—Thomas, Kayden, Horstemeyer & Risley, LLP

(57) ABSTRACT

A safety syringe has a barrel, a needle hub movably received in the barrel and having a hollow cone formed inside the needle hub and an annular cutout, a stopper having an engaging portion formed to correspond to the annular cutout and an extension integrally formed with the engaging portion and being slanted relative to the engaging portion, and a plunger having a first hook to correspond to the hollow cone and a second hook to correspond to the extension of the stopper. Engagement between the second hook and the extension of the stopper allows the stopper to be taken away from engagement with the needle hub and engagement between the first hook and the hollow cone allows the needle hub to be pulled inside the barrel and thus the syringe is able to be disposed of safely.

4 Claims, 7 Drawing Sheets

LABOR EFFICIENT SAFETY SYRINGE

BACKGROUND OF THE INVENTION

1. Field of the Invention

The present invention relates to a safety syringe, and more particularly to a labor efficient safety syringe. The syringe has a barrel, a plunger movably received in the barrel and provided with an extension, a first hook formed on a front portion of the extension and a second hook formed on a rear portion of the extension, a needle hub movably received in the barrel to engage with the first hook and a stopper movably received in the barrel to engage with the second hook. Engagement between the needle hub and the first hook and the engagement between the stopper and the second hook enable the needle together with the needle hub to be readily retracted into the barrel so that accidental damage to the paramedic is prevented.

2. Description of Related Art

A conventional syringe is shown in FIG. 7, and has a barrel (5), a needle hub (6) and a plunger (7).

The barrel (5) has a step (51) formed on an inner face thereof, the needle hub (6) has a flange (61) corresponding to the step (51) and having a diameter slightly larger than a diameter of the step (51). The plunger (7) has a stopper (71) and a hook (72) formed on a distal end of the plunger (7). The needle hub (6) further defines an annular cutout (62) to receive therein an engaging portion (711) of the stopper (71) and a retaining portion (63) formed to maintain the stopper (71) to be in engagement with the needle hub (6). The stopper (71) has an extension (712) extending out of the annular cutout (62) to correspond to the hook (72).

When the needle hub (6) is received in the barrel (5), because the diameter of the flange (61) is larger than the step (51), the diameter of the step (51) is enlarged so that the engagement between the needle hub (6) and the barrel (5) is secured. Then, the engaging portion (711) of the stopper (71) is received in the annular cutout (62) of the needle hub (6).

When the plunger (7) is pushed in the barrel (5) toward the needle hub (6), the hook (72) first passes over the extension (712) of the stopper (71) so as to complete an injection. Thereafter, when the user is pulling the needle hub (6) together with the needle (not shown) back into the barrel (5) in order to safely dispose of the syringe, the hook (72) engages with the extension (712) of the stopper (71) and then the user is able to pull the needle hub (6) together with the stopper (71) inward to the inside of the barrel (5).

However, problems often happen to the users when trying to dispose of the syringe of this type. That is, if the engagement between the flange (61) and the step (51) is too tight, the user will have difficulty pulling the needle hub (6) back into the barrel (5) and if the engagement between the flange (61) and the step (51) is too loose, the needle hub (6) will automatically fall into the barrel (5) when the user is trying to have medicine received inside the syringe. Accordingly, a precise calculation of the dimension of the needle hub (6), the plunger (7) and even the barrel (5) should be taken carefully so that a proper engagement among the needle hub (6), the plunger (7) and the barrel (5) is available.

To overcome the shortcomings, the present invention tends to provide an improved labor efficient safety syringe to mitigate and obviate the aforementioned problems.

SUMMARY OF THE INVENTION

The primary objective of the present invention is to provide an improved labor efficient safety syringe so that the user is able to readily pull the needle hub back into the barrel.

In order to accomplish the foregoing objective, the syringe has a barrel, a plunger movably received in the barrel and provided with an extension, a first hook formed on a front portion of the extension and a second hook formed on a rear portion of the extension, a needle hub movably received in the barrel to engage with the first hook and a stopper movably received in the barrel to engage with the second hook. Engagement between the needle hub and the first hook and the engagement between the stopper and the second hook enable the needle together with the needle hub to be readily retracted into the barrel so that accidental damage to the paramedic is prevented.

Other objects, advantages and novel features of the invention will become more apparent from the following detailed description when taken in conjunction with the accompanying drawings.

DETAILED DESCRIPTION OF THE PREFERRED EMBODIMENT

Figure 1:
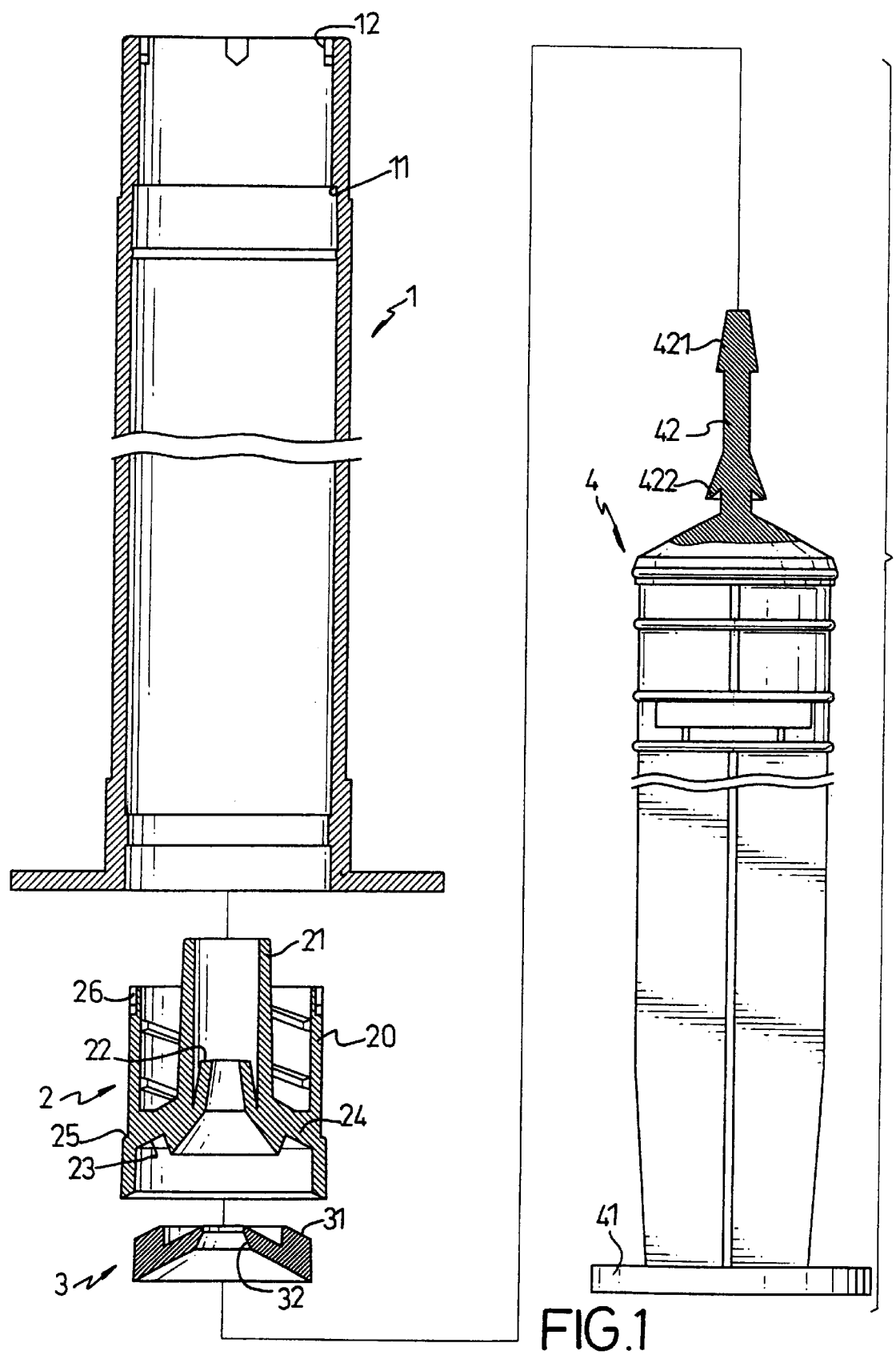
FIG. 1 is an exploded plan view showing the parts of the syringe of the present invention.

With reference to FIG. 1, the safety syringe in accordance with the present invention has a barrel (1), a needle hub (2), a stopper (3) and plunger (4).

The barrel (1) is hollow inside to receive therein the needle hub (2), the stopper (3) and the plunger (4). The barrel (10) further has multiple stops (12) formed on a distal end thereof to secure relative position between the barrel (1) and a needle hub (2), which will be described in detail in the following description.

The needle hub (2) is movably received in the barrel (1) and has a tubular connector (21) formed inside a body (20) for connection with a needle (not shown), a hollow cone (22) formed inside the tubular connector (21) and an annular cutout (23) defined in a bridge (24) which is formed to connect the tubular connector (21) to the body (20). The needle hub (2) further has multiple secondary stops (26) formed to correspond to the stops (12) of the barrel (1) so that when the needle hub (2) is inserted into the barrel (1), each of the stops (12) is aligned with a corresponding one of the secondary stops (26) so that the relative position between the barrel (1) and the needle hub (2) is secured, wherein the secondary stops (26) may be recesses and the stops (12) may be bosses.

The stopper (3) has an engaging portion (31) and an extension (32) integrally formed with the engaging portion

(31) and being slanted relative to the engaging portion (31). The engaging portion (31) has a dimension larger than a dimension of the annular cutout (23).

The plunger (4) has a thumb push (41) formed on a first end of the plunger (4) and a head (42) formed on a second end of the plunger (4) and having a first hook (421) formed on a front portion of the head (42) to correspond to the hollow cone (22) and a second hook (422) formed on a rear portion of the head (42) to correspond to the extension (32) of the stopper (3).

Figure 2:
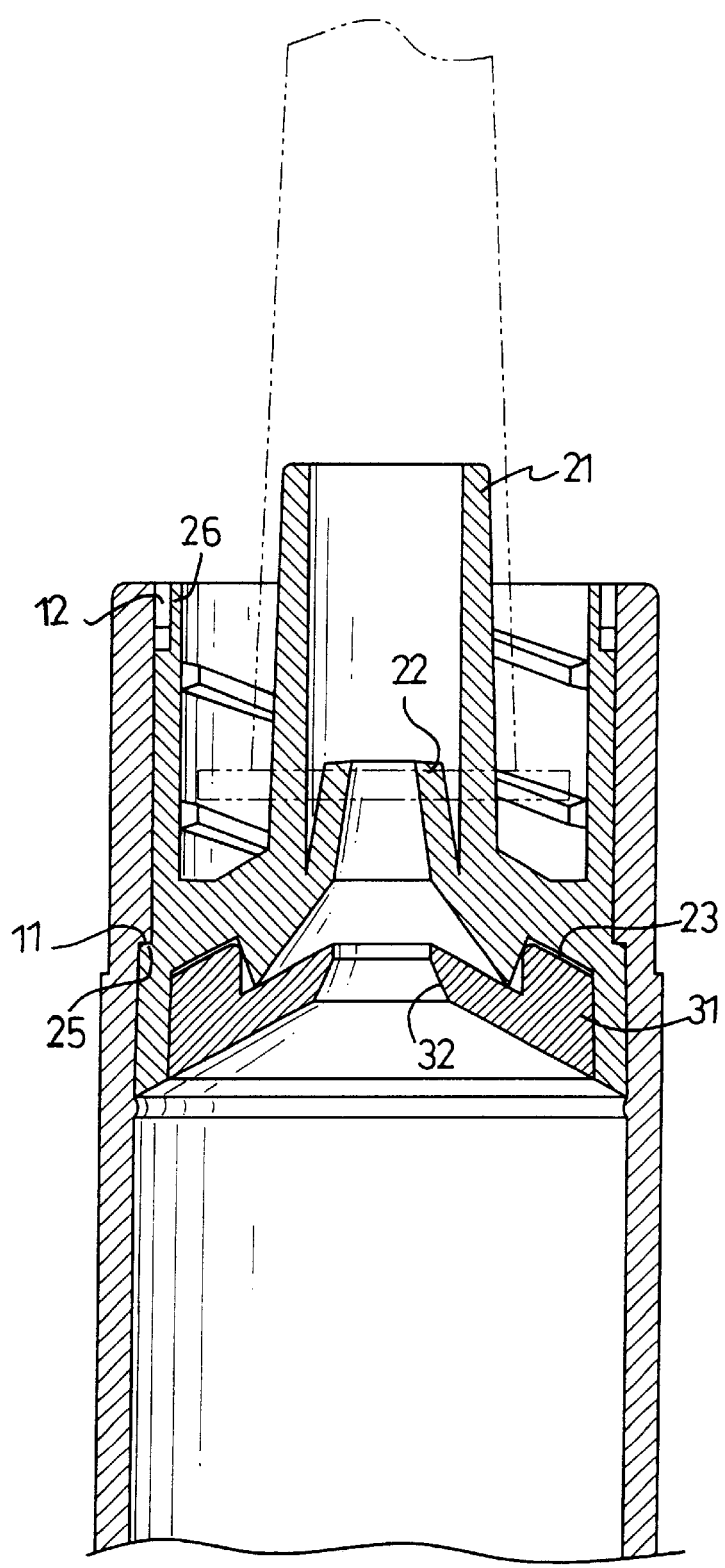
FIG. 2 is a cross sectional view showing an assembly among the barrel, the needle hub and the stopper.

With reference to FIG. 2, when the safety syringe of the present invention is in assembly, the needle hub (2) is first inserted into the barrel (1) to have the tubular connector (21) extended out of the hollow barrel (1) for engaging with a needle. Because of a flange (25) formed on an outer periphery of the barrel (2) and a step (11) formed on an inner periphery of the barrel (1), after the needle hub (2) is inserted into the barrel (1), the needle hub (2) is positioned inside the barrel (1). Then, the engaging portion (31) of the stopper (3) is force fitted into the annular cutout (23) of the needle hub (2) to enlarge the dimension of the annular cutout (23), which ensures that engagement between the inner periphery of the barrel (1) and an outer periphery of the needle hub (2) is water tight.

Because the extension (32) is inclined so that after the stopper (3) is inserted into the barrel (1) and the engaging portion (31) is received in the annular cutout (23), the extension (32) extends toward an inside of the hollow cone (22).

Figure 3:
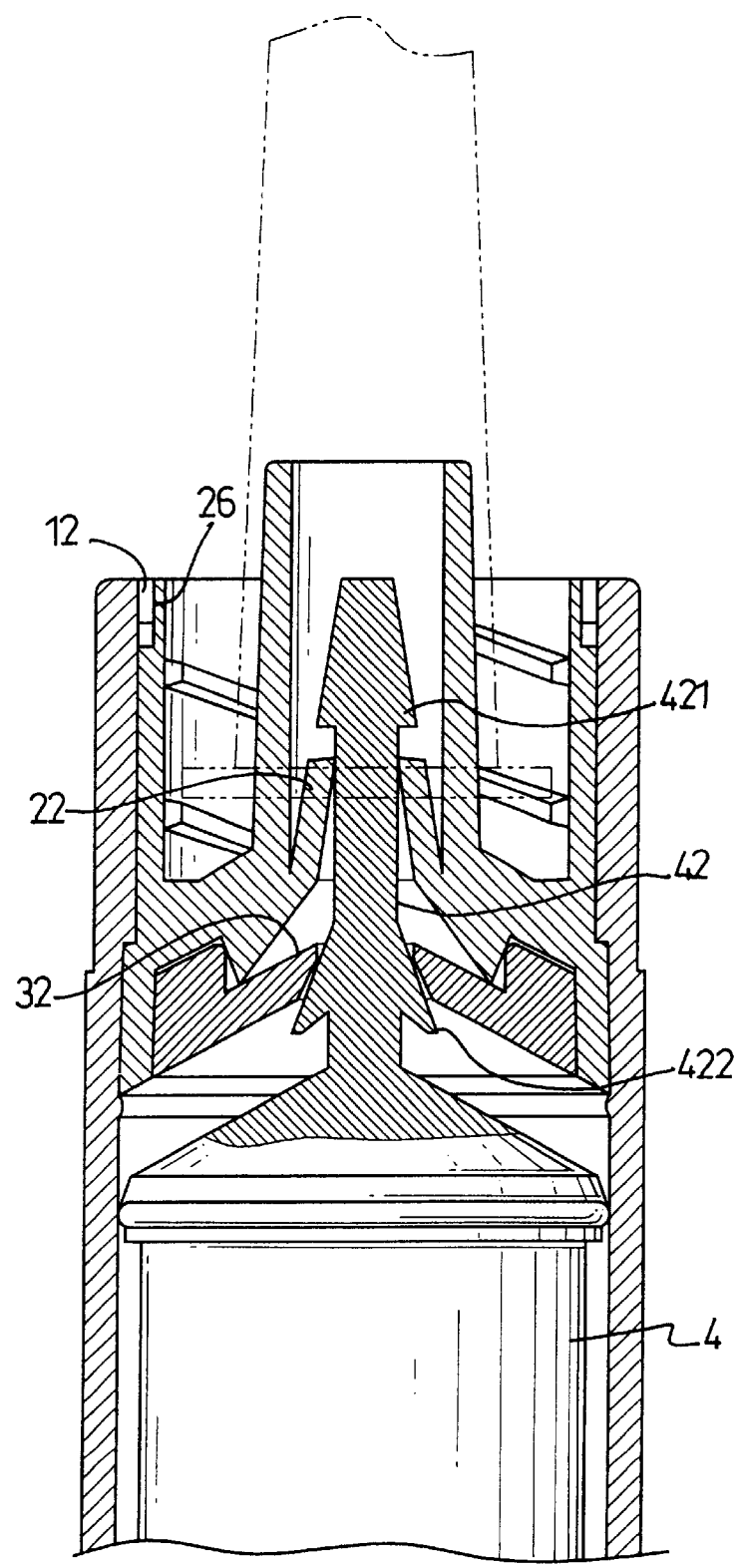
FIG. 3 is a cross sectional view showing the assembly in FIG. 2 together with the plunger to be inserted through the needle hub.
Figure 4:
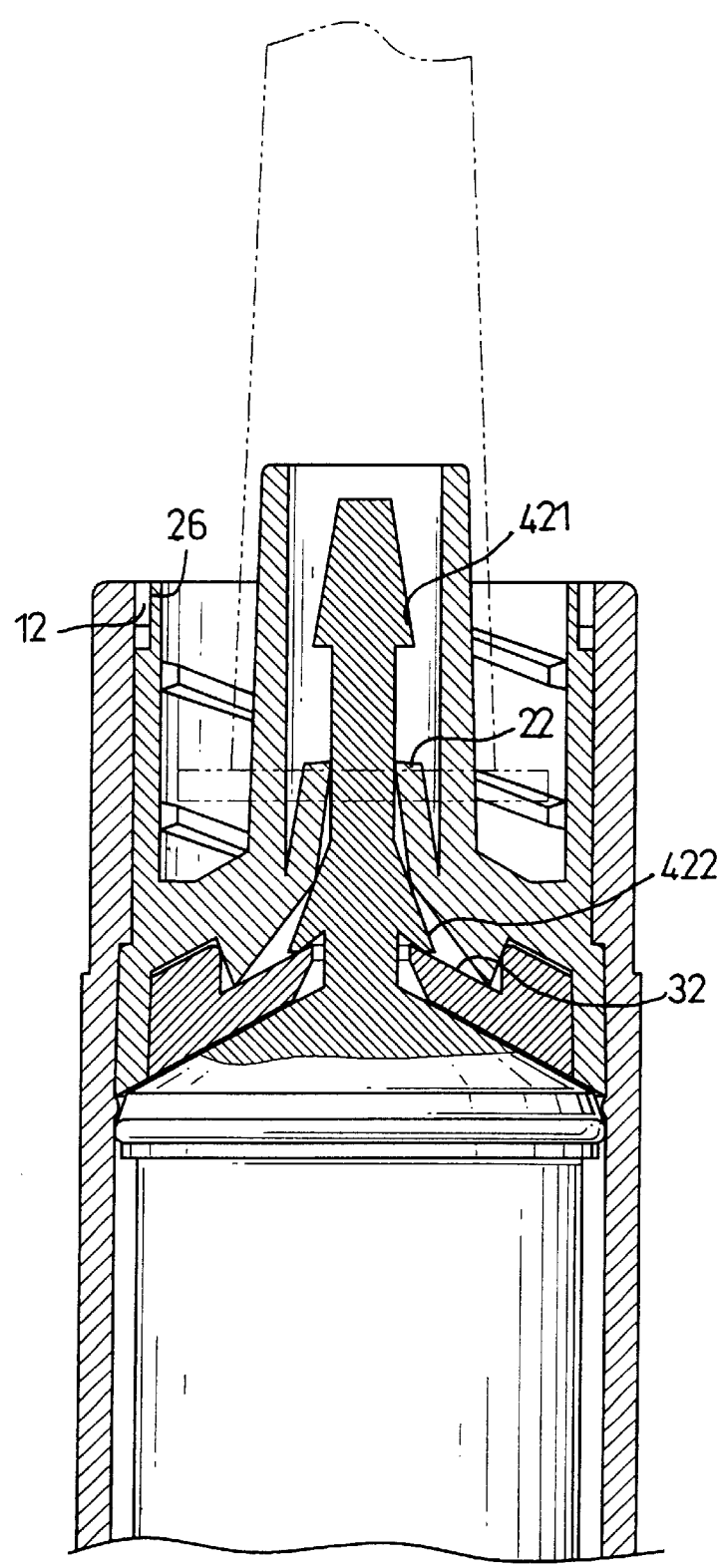
FIG. 4 is a cross sectional view showing the assembly in FIG. 2 together with the plunger inserted through the needle hub.

With reference to FIGS. 3 and 4, after the foregoing assembly, the syringe of the present invention is ready for use. Therefore, when the user is using the syringe to perform a hypodermic injection, the user extends the plunger (4) into the barrel (1). After the extension of the plunger (4) into the barrel (1), because the user needs to inject the medicine inside the barrel (1) to the recipient (the patient), the first hook (421) extends through the hollow cone (22). Thereafter, the second hook (422) extends over the extension (32) to completely expel the medicine out of the barrel (1). Basically, the foregoing description is the same as the conventional injection process. However, after the medicine is completely expelled out of the barrel (1), the first hook (421) leaves engagement with the hollow cone (22) and the second hook (422) engages with the extension (32) of the stopper (3).

Figure 5:
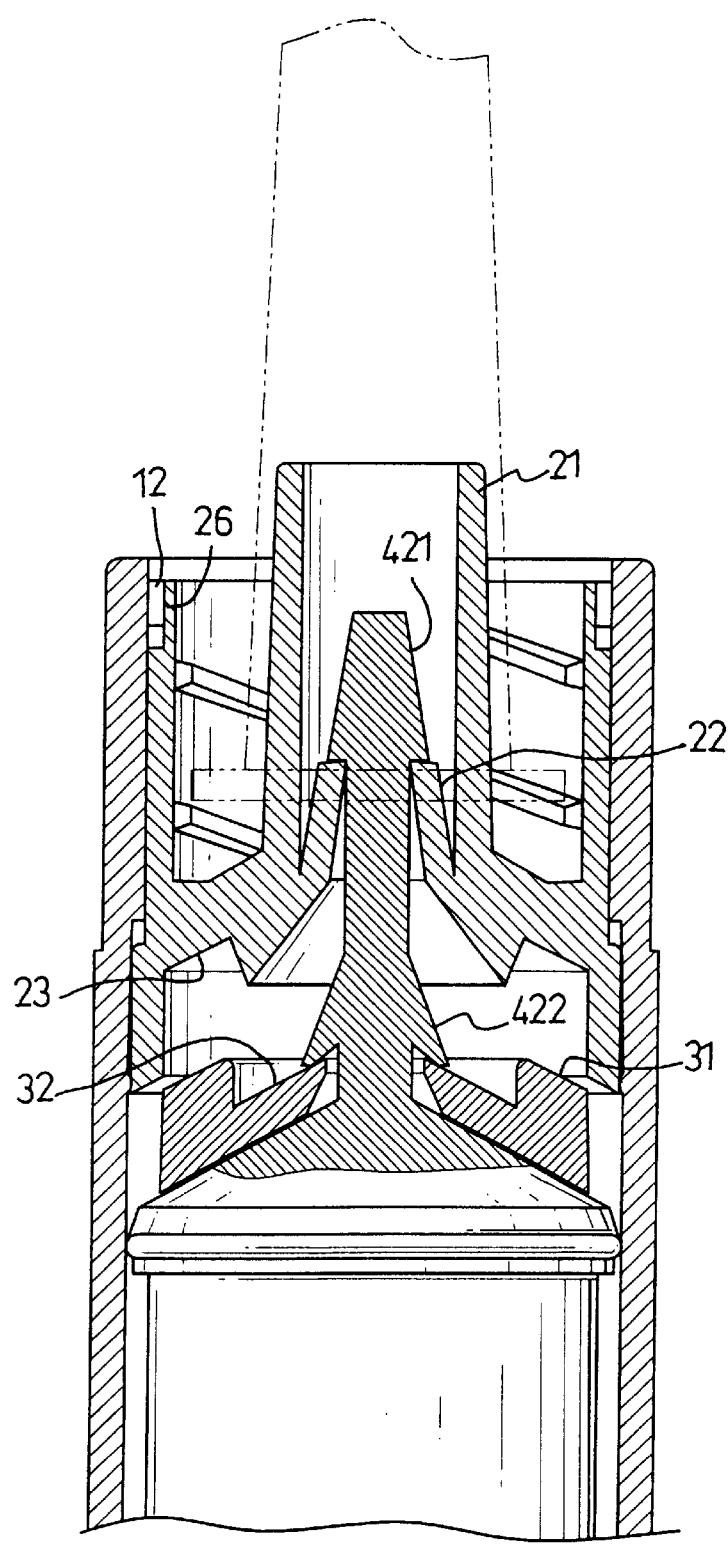
FIG. 5 is a schematic view showing the engagement of the plunger and the needle hub as well as the stopper.
Figure 6:
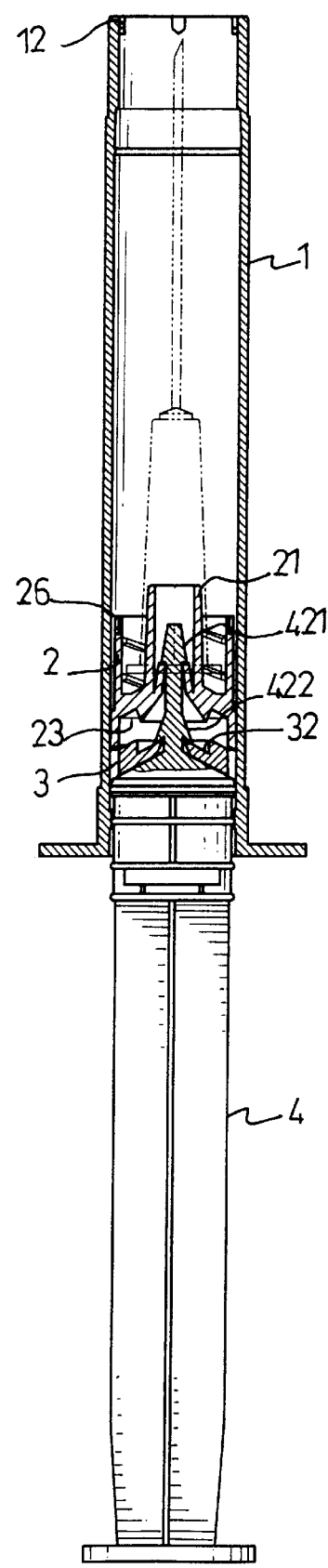
FIG. 6 is a schematic view showing that the entire needle hub together with the needle is pulled back into the barrel.
Figure 7:
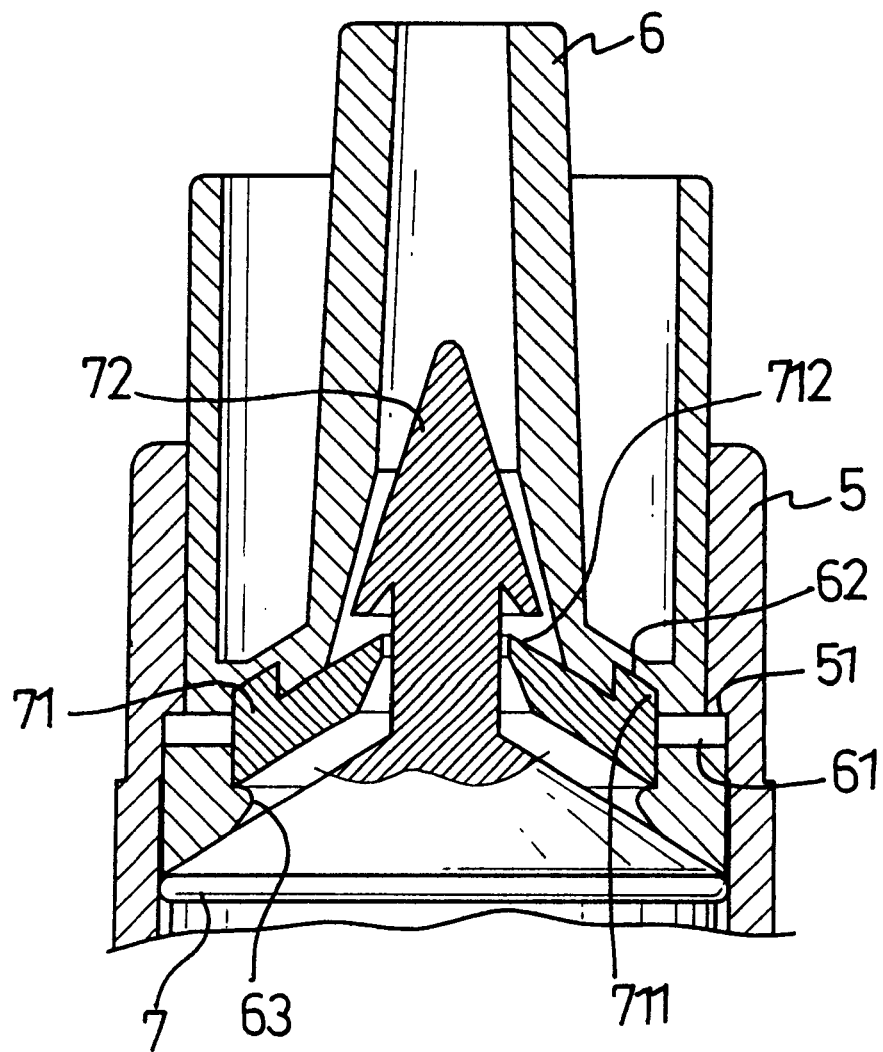
FIG. 7 is a cross sectional view showing the assembly of the barrel, the needle hub, the stopper and the plunger of a conventional safety syringe.

With reference to FIG. 5, after injection, in order to have the syringe of the present invention disposed of safely, the user pulls the plunger (4) inward into the barrel (1), which triggers engagement between the second hook (422) of the plunger (4) and the extension (32) of the stopper (3). Because the engagement between the second hook (422) and the extension (32) overcomes the friction engagement between the engaging portion (31) and the annular cutout (23), the stopper (3) is pulled away from engagement with the needle hub (2). After the disengagement, the user continues pulling backward the plunger (4) into the barrel (1) and eventually the first hook (421) of the plunger (4) engages with the hollow cone (22). Because the stopper (3) is already detached from the needle hub (2), the originally enlarged portion of the needle hub (2) recovers to its original dimension so that the rearward movement of the plunger (4) is able to readily pull the needle hub (2) into the barrel (1), as shown in FIG. 6.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. In a safety syringe having a barrel, a needle hub movably received in the barrel, a stopper detachably engaged with the needle hub and a plunger slidably received in the barrel and having a head extending out to engage with the stopper, wherein the improvements comprise:

the barrel is hollow inside to receive therein the needle hub, the stopper and the plunger and has a step formed on an inner periphery thereof, the needle hub is movably received in the barrel and has a tubular connector formed inside a body for connection with a needle, a hollow cone formed inside the tubular connector and an annular cutout defined in a bridge which is formed to connect the tubular connector to the body, the stopper has an engaging portion formed to correspond to the annular cutout and an extension integrally formed with the engaging portion and being slanted relative to the engaging portion, the plunger has a thumb push formed on an end relative to the head of the plunger, a first hook adapted to be formed on a front portion of the head to correspond to the hollow cone and a second hook adapted to be formed on a rear portion of the head to correspond to the extension of the stopper, whereby after injection rearward movement of the plunger first allows engagement between the second hook and the extension of the stopper so that the stopper is taken away from engagement with the needle hub and then engagement between the first hook and the hollow cone so that the needle hub is pulled inside the barrel and thus the syringe is able to be disposed of safely.

2. The safety syringe as claimed in claim 1, wherein the engaging portion has a dimension larger than a dimension of the annular cutout so that when the engaging portion is received in the corresponding annular cutout, a dimension of the needle hub is partially enlarged so as to ensure engagement between an outer periphery of the needle hub and an inner periphery of the barrel is fluid-tight.

3. The safety syringe as claimed in claim 1, wherein the hollow barrel further has multiple stops formed on a distal end of the hollow barrel to correspond to multiple secondary stops formed on an inner face of the needle hub so that after the needle hub is received in the hollow barrel, the stops and the secondary stops are aligned with one another and relative position between the hollow barrel and the needle hub is secured.

4. The safety syringe as claimed in claim 2, wherein the hollow barrel further has multiple stops formed on a distal end of the hollow barrel to correspond to multiple secondary stops formed on an inner face of the needle hub so that after the needle hub is received in the hollow barrel, the stops and the secondary stops are aligned with one another and relative position between the hollow barrel and the needle hub is secured.

* * * * *